United States Patent [19]

Tsuno

[11] Patent Number: 4,708,434
[45] Date of Patent: Nov. 24, 1987

[54] FIBERSCOPE WITH BENDING MECHANISM

[75] Inventor: Koichi Tsuno, Osaka, Japan

[73] Assignee: Sumitomo Electric Industries, Ltd., Osaka, Japan

[21] Appl. No.: 739,258

[22] Filed: May 30, 1985

[30] Foreign Application Priority Data

May 30, 1984 [JP] Japan .................... 59-112123

[51] Int. Cl.$^4$ ............................ G02B 23/26
[52] U.S. Cl. .................... 350/96.26; 128/6
[58] Field of Search ........... 350/96.25, 96.26; 128/6, 7, 8, 9; 604/96, 97

[56] References Cited

U.S. PATENT DOCUMENTS

| | | | |
|---|---|---|---|
| 3,572,325 | 3/1971 | Bazeli et al. | 128/6 |
| 3,583,393 | 6/1971 | Takahashi | 128/4 |
| 3,610,231 | 10/1971 | Takahashi et al. | 128/6 |
| 3,690,769 | 9/1972 | Mori | 350/96.26 X |
| 3,788,304 | 1/1974 | Takahashi | 350/96.25 X |
| 3,960,143 | 6/1976 | Terada | 128/4 |
| 4,569,335 | 2/1986 | Tsuno | 128/6 |
| 4,620,769 | 11/1986 | Tsuno | 350/96.26 |

FOREIGN PATENT DOCUMENTS

| | | |
|---|---|---|
| 1102341 | 3/1961 | Fed. Rep. of Germany . |
| 1086821 | 10/1967 | United Kingdom . |

*Primary Examiner*—John Lee
*Assistant Examiner*—John Ngo
*Attorney, Agent, or Firm*—Sughrue, Mion, Zinn, Macpeak & Seas

[57] ABSTRACT

A fiberscope having a freely bendable tip and having a reduced weight and diameter. Two spaced cylindrical casted sections are provided at the forward end of the fiberscope, and the image fiber, light guides for transmitting illuminating light, and manipulating wires are inserted through the two cylindrical casted sections. Each of the manipulating wires may be inserted through a tube in coil form.

7 Claims, 6 Drawing Figures

FIBERSCOPE WITH BENDING MECHANISM

BACKGROUND OF THE INVENTION

The present invention relates to a fiberscope using an image fiber that enables direct transmission of an image through a bundle of aligned filaments. More particularly, the invention relates to such a fiberscope having a freely bendable tip.

Most fiberscopes using an image fiber, inter alia gastroscopes, require frequent change in the direction of the imaging section by external manipulation. The conventional mechanism for meeting this requirement is illustrated in FIG. 5. As seen in that drawing, an image fiber 1 is surrounded by a plurality of node rings 2 which are caused to abut against each other with an intervening central spherical fulcrum 3. Manipulating wires 4 are inserted through the ring nodes 2. The manipulating wires are controlled by the mechanism shown in FIG. 6 so as to permit free bending of the image fiber 1.

One major problem with the fiberscope having the construction described above is its relatively large thickness that results from the use of the node rings 2.

With the recent development of new processes for the production of image fibers, it has become possible to fabricate a very fine and long fiberscope. However, in order to expand the use of such new fiberscope, it is necessary to develop a tip manipulating arrangement adapted to this new fiberscope which is free from the defects mentioned above.

SUMMARY OF THE INVENTION

The principal object, therefore, of the present invention is to provide a fiberscope equipped with tip manipulating means that satisfies these needs.

In order to solve the problems with the conventional fiberscope and to achieve the object described above, the present invention replaces the conventional node rings by a flexible rubber tube that is used as a cover for the bending portion and through which the manipulating wires are inserted.

DESCRIPTION OF THE PREFERRED EMBODIMENTS

Figure 1:
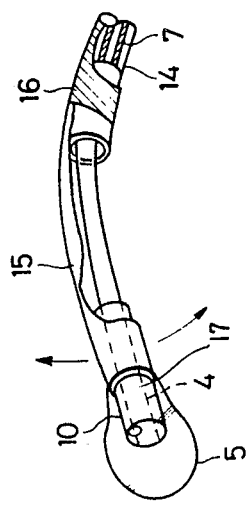
FIG. 1 shows one embodiment of the mechanism for realizing the bending of the tip of the fiberscope in accordance with the present invention.
Figure 2:
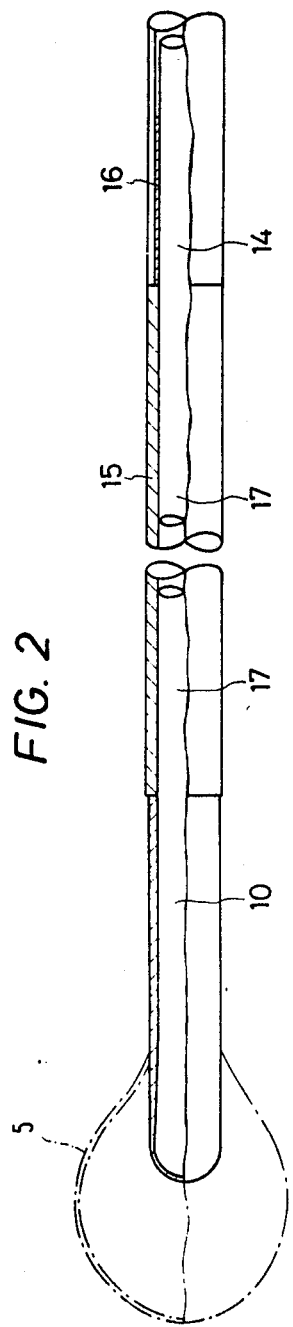
FIG. 2 shows an example of the construction of the tip of the same fiberscope.
Figure 3:
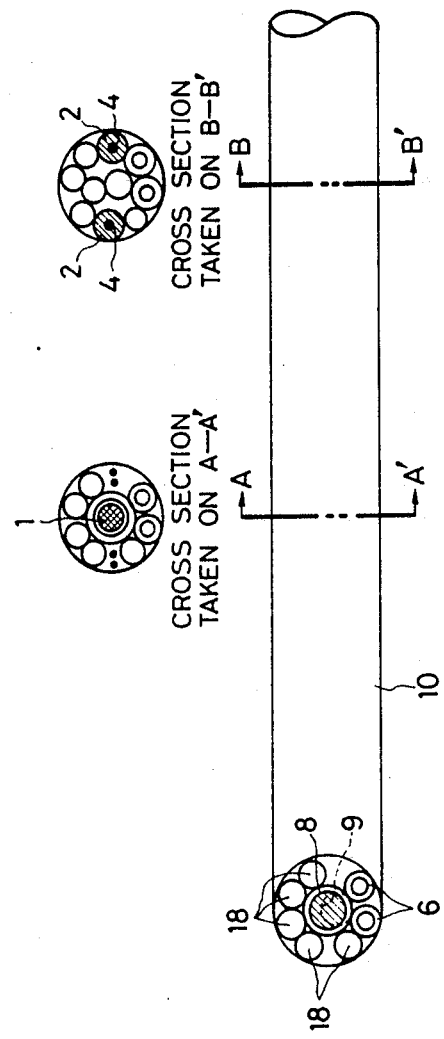
FIG. 3 shows an example of the tip casted section of the same fiberscope.

A preferred embodiment of a fiberscope of the present invention is shown in FIGS. 1 to 4. This fiberscope is especially designed for viewing the inner walls of the heart. In order to ensure a wide field of view and eliminate any opaque blood, a transparent balloon 5 is provided at the forward end of the fiberscope as shown in FIG. 1. As depicted in FIG. 3, the internal components of the scope are an image fiber 1, light-guiding plastic fiber bundles 18, and balloon expanding or contracting tubes 6. At the tip of the image fiber 1 is provided a sleeve 8 which is connected to an imaging lens 9. In order to ensure easy bending of the fiber, two manipulating wires 4 sheathed in tubes in a coil form 7 are provided diametrically in the cross section of the fiber. The tubes 7 are made of a material such as stainless steel that ensures good slip on the manipulating wires 4.

Figure 4:
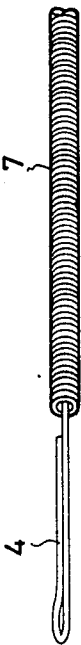
FIG. 4 illustrates a manipulating wire sheathed in a tube in coil from used in the fiberscope of the present invention.
Figure 5:
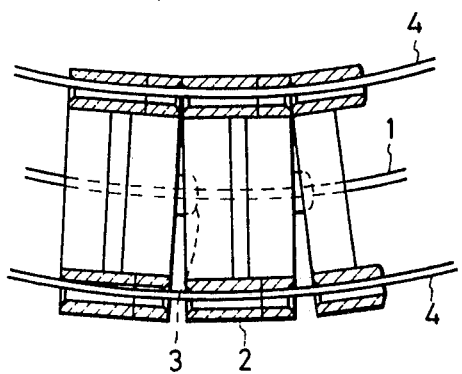
FIG. 5 illustrates the conventional bending mechanism.
Figure 6:
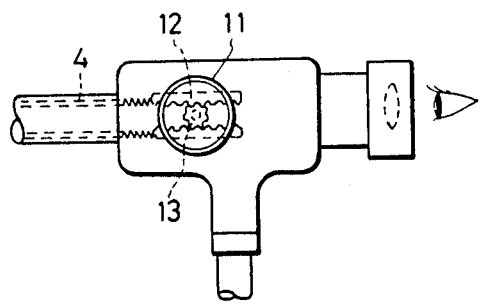
FIG. 6 shows the manipulation wire control mechanism at the image receiving section of the same fiberscope.

The device shown in FIG. 1 (which does not show the image fiber and light guide), has an assembly of elements 17 (including the imaging lens and other tip-forming elements) that are casted and fixed in an epoxy resin or other suitable materials, thereby providing a tip casted section 10. The tubes 7 in a coil form extend halfway through an intermediate casted section 14 and only the manipulating wires 4 extend to the tip casted section 10. As shown in FIGS. 3 and 4, the tip of each manipulating wire 4 is folded back and fixed within the tip casted section. In the embodiment shown in FIG. 1, the intermediate casted section 14 is spaced from the tip casted section 10 and has the assembly of elements 17 (shown in FIG. 2) casted and fixed therein. The assembly of elements 17 is held free between the two casted portions. That part of the image fiber which is between these two casted sections is covered with a rubber tube 15 made of silicone rubber or other material that satisfy the requirements: (1) sufficient resiliency to provide an adequate resistance against the bending forces exerted by manipulation with the wires 4, and (2) sufficient resiliency to provide an adequate resistance against radial expansion of the assembly of elements 17. With the construction described above, the outer diameter of the cable section of the fiberscope in accordance with the present invention can be reduced to a dimension as small as 2.8 mm. The manipulating wires 4 have outside and inside diameters of approximately 0.53 mm and 0.19 mm, respectively. The bending mechanism incorporated in the scope of the present invention permits free bending through $\pm 45\frac{1}{4}$ under a tension of about 1.4 kg.

FIG. 2 shows the construction of the tip portion of the fiberscope in accordance with the present invention, and FIG. 3 illustrates the construction of the tip casted section 10.

In order to provide greater slip on the manipulating wires, the inner surfaces of the tubes 7 in coil form may be coated with a polyethylene tetrafluoride resin such as Teflon R. Bending in more than two directions may be achieved by using a greater number of manipulating wires.

As described in the foregoing, the fiberscope of the present invention replaces the conventionally used node rings by a flexible rubber tube that provides an outer cover for the bending section and through which the manipulating wires are inserted. The bending mechanism incorporated in the fiberscope does not result in an increase in diameter; instead, this mechanism contributes to a reduction in the cost and weight of the bending portion.

I claim:

1. A fiberscope comprising a cover tube, an image fiber disposed within said cover tube and a bending mechanism adjacent a forward end of the fiber scope, said bending mechanism including a first cylindrical cast section having passage means for said fiber partially secured to said cover tube, a second cylindrical cast section having passage means for said fiber secured at the forward end of the fiberscope, and a rubber tube of resilient material having greater flexibility than said cover tube secured on said first section adjacent one end of said rubber tube and secured on said second section adjacent the other end of said rubber tube with the second section being disposed in spaced relation from said first section, said image fiber having an image lens secured on an end thereof adjacent said second section and said fiberscope further comprising light guide means for transmitting illuminating light and manipulating wires extending through said cover tube, said rubber tube and said cast sections with said manipulating wires being secured to said second cast section to move said second section relative to said first section.

2. The fiberscope according to claim 1, wherein each of said manipulating wires is inserted through a tube in a coil form, said tube having inner surfaces provided with a coat of polyethylene tetrafluoride resin.

3. The fiberscope according to claim 1, wherein a forward end of each manipulating wire is folded back and fixed to said second cast section.

4. The fiberscope according to claim 1, wherein said resilient material comprises silicone rubber.

5. The fiberscope according to claim 1, wherein said manipulating wires are provided diametrically opposite in a cross section of said fiberscope.

6. The fiberscope according to claim 1, further comprising a transparent balloon (5) disposed at the forward end of the fiberscope.

7. The fiberscope according to claim 1, further comprising; a tube (7), in coil form, housing each of said manipulating wires, said tube being secured at one end to the first cast section.

* * * * *